United States Patent
Hernandez-Guerra

(10) Patent No.: US 6,208,712 B1
(45) Date of Patent: Mar. 27, 2001

(54) PORTAL IMAGE WITHIN A VIRTUAL WEDGE TREATMENT

(75) Inventor: Francisco M. Hernandez-Guerra, Concord, CA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/172,107

(22) Filed: Oct. 13, 1998

(51) Int. Cl.$^7$ .................................................. G21F 5/04
(52) U.S. Cl. ......................... 378/150; 378/65; 378/147; 250/492.1
(58) Field of Search ................... 378/65, 147, 149, 378/150, 151, 152; 250/492.1, 492.3, 505.1

(56) References Cited

U.S. PATENT DOCUMENTS

| | | |
|---|---|---|
| 5,138,647 | 8/1992 | Nguyen et al. .................. 378/189 |
| 5,148,032 | 9/1992 | Hernandez .......................... 378/151 |
| 5,563,925 | 10/1996 | Hernandez .......................... 378/150 |
| 5,619,042 * | 4/1997 | Hughes ................................ 378/150 |
| 5,668,847 * | 9/1997 | Hernandez .......................... 378/150 |
| 5,684,854 * | 11/1997 | Hughes ................................ 378/151 |
| 5,724,403 * | 3/1998 | Siochi et al. ....................... 378/150 |
| 5,847,403 * | 12/1998 | Hughes et al. ..................... 378/150 |

* cited by examiner

Primary Examiner—Robert H. Kim
Assistant Examiner—Drew A. Dunn

(57) ABSTRACT

Method and system aspects for utilizing portal images in a virtual wedge treatment during radiation treatment by a radiation-emitting device are described. In a method aspect, and system for achieving same, the method includes utilizing an image dose with a static jaw gap position to initiate a virtual wedge treatment with portal imaging. The method further includes continuing with the virtual wedge treatment from a reduced jaw gap position with a dynamic dose and dynamic jaw positioning. In addition, the virtual wedge treatment in completed with a static dose in the static jaw gap position.

11 Claims, 4 Drawing Sheets

Case 1) 3MV, 50 MU, 60 degree, 50 mm

MU10 := 5
β := 6
μ := .0060
s := 5

$$\alpha := \beta \cdot \frac{x}{18}$$

DoseRate :=
DRCV := 600

$$MU := MU10 \cdot e^{\frac{\mu \cdot s \cdot \tan(\alpha)}{2}}$$
MU = 64.975

$$MUjaw := MU \cdot \left(1 - e^{\mu \cdot s \cdot \tan(\alpha)}\right)$$

MUjaw = 26.498
MUimage and MUstatic := MU − MUjaw
MUimage and MUstatic = 38.477

The 50 mm Virtual Wedge require 38.5 MU at Dmax and Central Axis.

FIG. 5a

Case 2) 3MV, 50 MU, 60 degree, 50 mm

MU10 := 5
β := 6
μ := .0060
s := 20

$$\alpha := \beta \cdot \frac{x}{18}$$

DoseRate :=
DRCV := 600

$$MU := MU10 \cdot e^{\frac{\mu \cdot s \cdot \tan(\alpha)}{2}}$$
MU = 142.581

$$MUjaw := MU \cdot \left(1 - e^{\mu \cdot s \cdot \tan(\alpha)}\right)$$

MUjaw = 26.498
MUimage and MUstatic := MU − MUjaw
MUimage and MUstatic = 17.534

The 200 mm Virtual Wedge require 17.5 MU at Dmax and Central Axis.

FIG. 5b

PORTAL IMAGE WITHIN A VIRTUAL WEDGE TREATMENT

FIELD OF THE INVENTION

The present invention relates to radiation treatment devices, and more particularly, to portal images within a virtual wedge treatment by a radiation treatment device.

BACKGROUND OF THE INVENTION

Radiation-emitting devices are generally known and used for radiation therapy in the treatment of patients, for example. Typically, a radiation therapy device includes a gantry which can be swiveled around a horizontal axis of rotation in the course of a therapeutic treatment. A linear accelerator is located in the gantry for generating a high-energy radiation beam for therapy. This high radiation beam can be an electron radiation or photon (X-ray) beam. During treatment, the radiation beam is provided on one zone of a patient lying in the isometer of gantry rotation.

The goal of radiation treatment planning is to maximize the dose to the target volume while protecting radiation sensitive healthy tissue. The X-ray bean intensity often varies over the treatment field by placing an X-ray absorber in the beam's path. This allows the target volume to be placed in regions of high beam intensity, while the surrounding radiation sensitive tissue is protected by placement in low intensity regions. A simple example is a wedge-shaped isodose distribution, which has been found to be clinically useful in treatment plans.

One frequently used method is to place a physical wedge accessory (i.e., a wedge-shaped absorber) in the X-ray beam path that exponentially decreases the beam intensity laterally across the treatment field. A desirable wedge-shaped isodose distribution results. The "toe" of the wedge (i.e., where the thickness of the wedge is the smallest) produces the high beam intensity region, since this portion of the beam has the least attenuation.

The use of the physical wedge accessory has some negative side effects, however. The primary beam intensity is reduced at the target volume; thus, treatment times are increased. Further, scattering of the beam outside the treatment field causes additional dose to be delivered outside the target volume. It also introduces a spatial energy dependence (i.e., hardness) to the beam, affecting the depth at which the radiation is absorbed across the treatment field. Additional time and effort are required to design, validate, manufacture, install/remove, and store the accessories. In addition, only a limited number of wedge angles are available.

The virtual wedge function integrated into some treatment devices, such as MEVATRON and PRIMUS systems from Siemens Corporation, New Jersey, is used to achieve an accumulated dose profile and isodose distribution similar to that of a physical wedge accessory. The virtual wedge function is accomplished by controlling the travel of a secondary collimator jaw and the X-ray beam intensity during irradiation. The virtual wedge scheme eliminates most of the problems associated with the physical wedge.

A further feature of radiation therapy involves portal images, which are commonly used in radiation therapy to verify and record the patient tumor location. Portal images include manual (film) and electronic images (EPI) taken before or after the treatment. Electronic portal images (EPI), when taken before the treatment, give the therapist the opportunity of correcting for minor patient positioning errors before treatment. Further, EPI allows therapists to take images remotely without going inside the treatment room.

Conventional radiation therapy technique typically utilize field sizes in the range of 5 to 30 cm, and doses per fraction in the range of 70 to 200 MU (monitor units). With portal images taken once a week and requiring up to 10 MU each, the portal image dose does not introduce a significant impact on the original dosimetric calculations. However, with intensity modulation techniques (IMRT), the treatment fields and doses are calculated to be more geometrically and dosimetrically precise. Treatment fields are decomposed into dose segments, which are smaller than in conventional treatments. When fields are small, dosimetric output factors are reduced as well. Therefore, portal image doses can affect the original dosimetric plan of IMRT.

When the treatment technique is fixed and using EPI, the problem can be resolved by including the dosimetric effect of the portal image into the initial dosimetric calculations at the treatment planning level. For virtual wedge treatment, the dynamic nature of the therapy restricts the use of portal images in assisting repositioning of the patient before treatment.

In accordance with known, prior art virtual wedge treatments, when programming the field size, all jaws are moved to their preset positions, as shown in FIG. 1a. When the treatment is accepted by a therapist, the jaw 30 acting as the dynamic jaw closes to a minimum gap position, usually approximately 0.5 centimeters (cm) from the stationary or opposite jaw 32, as shown in FIG. 1b. The dynamic jaw 30 then automatically opens at a constant average speed to the initial gap position, typically about 1 cm from the opposite jaw 32. As the dynamic jaw 30 opens, a pre-treatment jaw calibration speed test is performed, as shown in FIG. 1c, and an interlock is generated if this test fails. Once the dynamic jaw 30 reaches the initial gap position and no interlocks are asserted, the system is ready to begin treatment.

When the therapist starts the treatment, the initial dose is delivered with the dynamic jaw 30 in its initial gap position and is referred to as $MU_{gap}$, as shown in FIG. 1d. Once the $MU_{gap}$ has been delivered, the dynamic jaw 30 is opened at a constant average speed to its final/preset position, while simultaneously the dose rate is varied as a function of the jaw position. FIG. 1e illustrates the dynamic portion with the dose delivered as the jaw 30 travels as $MU_{trav}$. The remaining dose is delivered with the dynamic jaw 30 in its idle, final position as shown in FIG. 1f with a dose of $MU_{idle}$. While a portal image could be taken during the idle portion of the virtual wedge treatment of FIG. 1f, there would be no chance to correct patient positioning errors, since the idle portion occurs after the majority of the treatment dose has been delivered.

Accordingly, what is needed is a method and system for effectively utilizing portal images in a virtual wedge treatment.

SUMMARY OF THE INVENTION

The present invention provides method and system aspects for utilizing portal images in a virtual wedge treatment during radiation treatment by a radiation-emitting device. In a method aspect, and system for achieving same, the method includes utilizing an image dose with a static jaw position to initiate a virtual wedge treatment with portal imaging. The method further includes continuing with the virtual wedge treatment from a reduced gap position with a dynamic dose and dynamic jaw positioning. In addition, the virtual wedge treatment in completed with a static dose in the static jaw position.

Through the present invention, a straightforward technique of radiation delivery is provided that allows portal images to be taken before a dynamic portion of a virtual wedge treatment. Effective utilization of portal images produces beneficial assistance in ensuring proper patient positioning for the radiation therapy. These and other advantages of the aspects of the present invention will be more fully understood in conjunction with the following detailed description and accompanying drawings.

BRIEF DESCRIPTION OF THE DRAWINGS

FIGS. 5a and 5b illustrate examples of virtual wedge treatment calculations in accordance with the present invention.

DETAILED DESCRIPTION OF THE INVENTION

The present invention relates to effective utilization of portal images within a virtual wedge treatment. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. In the following, the invention is described with primary reference to a system for delivering X-ray radiation to a field of a patient, and for delimiting the field using at least one movable plate in the beam path from a radiation source. This is by way of example. Thus, the present invention is not intended to be merely limited to the embodiment shown but is to be accorded the widest scope consistent with the principles and features described herein.

Figure 1A:
FIGS. 1a, 1b, 1c, 1d, 1e, and 1f illustrate a basic virtual wedge treatment of the prior art.
Figure 1B:
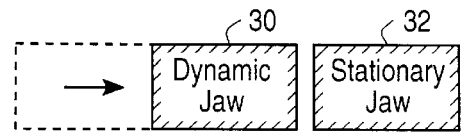
Figure 1C:
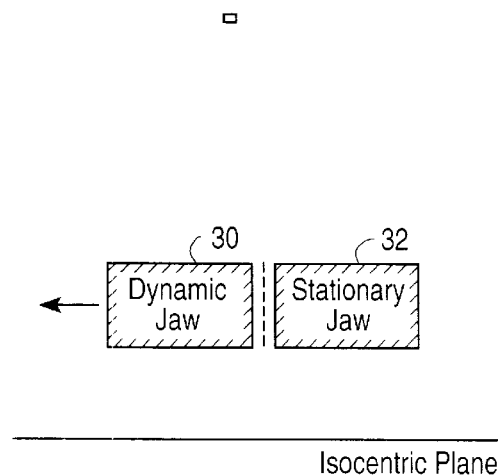
Figure 1D:
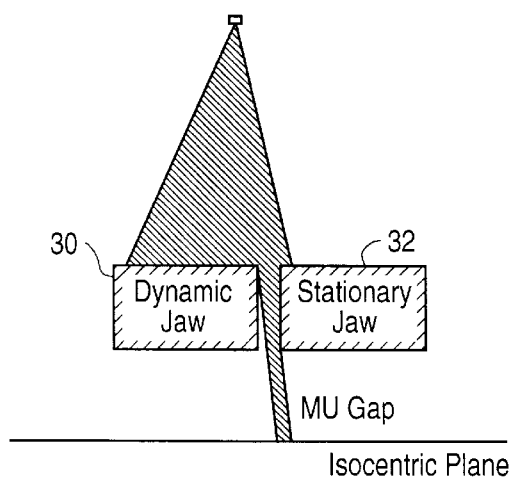
Figure 1E:
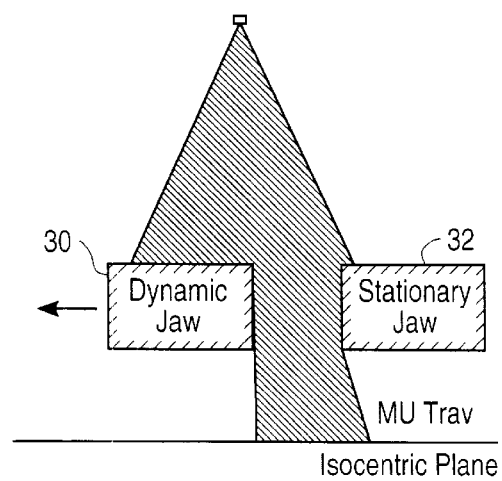
Figure 1F:
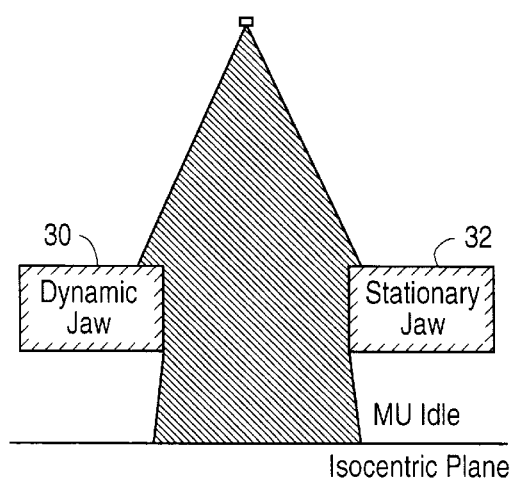
Figure 2:
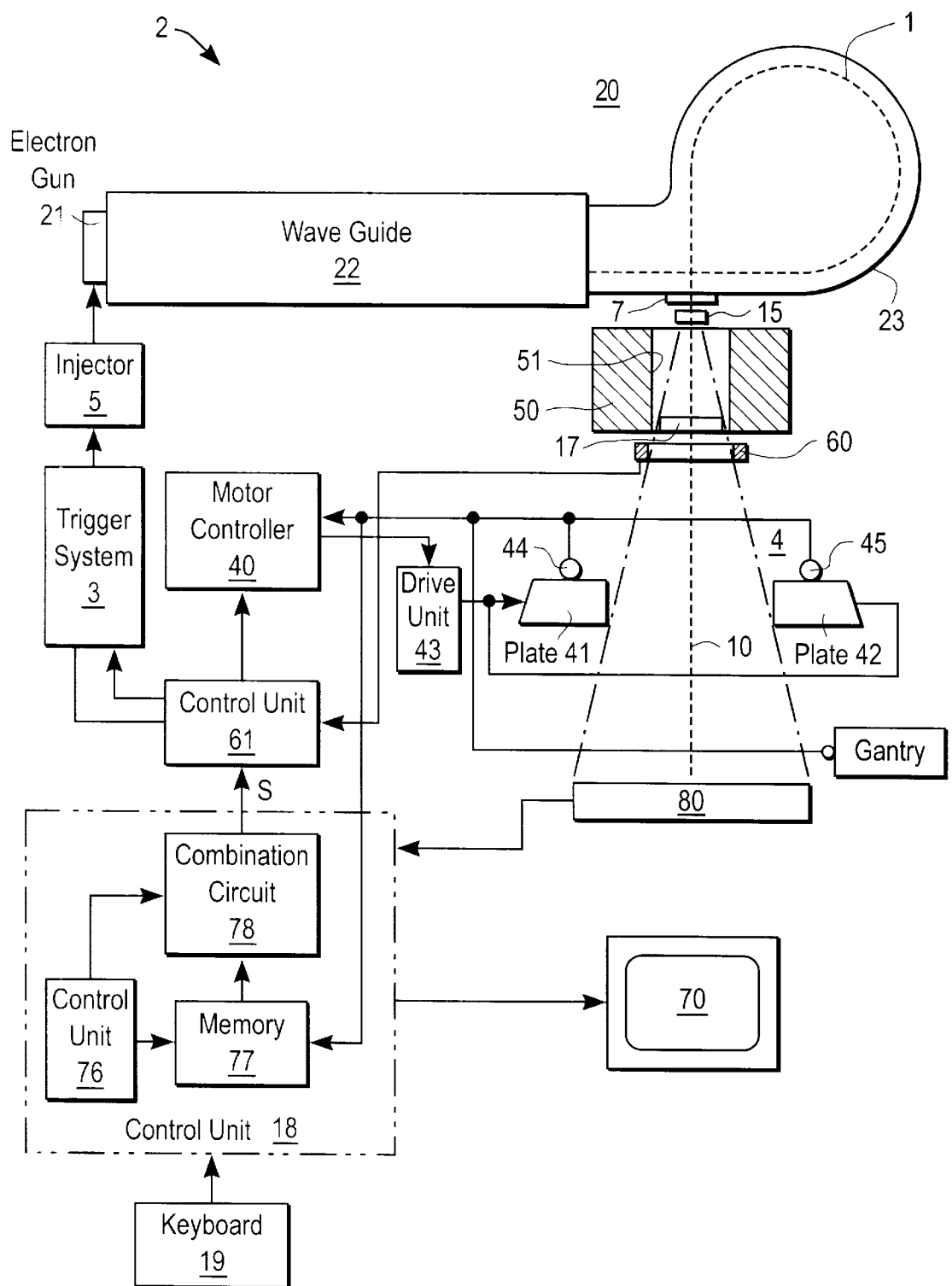
FIG. 2 is a block diagram illustrating portions of a processing unit, control unit, and a beam generation system in a radiation treatment device for a preferred embodiment of the present invention.

FIG. 2 shows a portion of an illustrative radiation treatment device 2 and portions of a treatment processing unit in detail. An electron beam 1 is generated in an electron accelerator 20. Accelerator 20 comprises an electron gun 21, a wave guide 22, and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, the beam is sent through a measuring chamber 60, in which the dose is ascertained. If the scattering foils are replaced by a target, the radiation beam is an X-ray beam.

Plate arrangement 4 comprises a pair of aperture plates 41 and 42 and an additional pair of aperture plates (not shown) arranged perpendicular to plates 41 and 42. In order to change the size of the irradiated field, the aperture plates 41 and 42 can be moved with respect to axis 10 by a drive unit 43 which is indicated in FIG. 2 only with respect to plate 41. Drive unit 43 comprises an electric motor which is coupled to plates 41 and 42 and which is controlled by a motor controller 40. Position sensors 44 and 45 are also coupled to plates 41 and 42, respectively, for sensing their positions.

The area of a patient that is irradiated is known as the field. As is well known, plates 4 are substantially impervious to the emitted radiation. They are mounted between the radiation source and patient in order to delimit the field. Areas of the body, for example, healthy tissue, are therefore subjected to as little radiation as possible, and preferably to none at all. As previously described, with at least one of the plates movable, the distribution of radiation over the field need not be uniform (one region can be given a higher dose than another); further, with the gantry able to be rotated, different beam angles and radiation distributions are allowed without having to move the patient around.

A central treatment processing or control unit is usually located apart from radiation treatment device 2 in a different room to protect the therapist from radiation. Treatment processing unit includes an output device, such as at least one visual display unit or monitor 70, and an input device, such as a keyboard 19, although data can be input also through data carriers, such as data storage devices. The treatment processing unit is typically operated by the therapist who administers actual delivery of a radiation treatment as prescribed by an oncologist. By utilizing keyboard 19, or other input device, the therapist enters into a control unit 76 of the treatment processing unit the data that defines the radiation to be delivered to the patient. On the screen of a monitor 70, various data can be displayed before and during the treatment.

Central processing unit 18, included in treatment processing unit, is connected with the input device, e.g., keyboard 19, for inputting the prescribed delivery of the radiation treatment and with a dose control unit 61 that generates the desired values of radiation for the controlling trigger system 3. Trigger system 3 suitably adapts the pulse repetition frequency or other parameters to change the radiation output. A digital dosimetry system is particularly advantageous in order to more easily control the digital output of central processing unit 18. Central processing unit 18 suitably includes a control unit 76 for controlling execution of the treatment program in conjunction with memory 77 and a combination circuit 78 which suitably receives signals from the control unit 76 and memory 77 for combination to produce a set signal, S, that identifies a dose rate for dose rate control unit 61.

Further included in the treatment system is a portal imaging device 80. A portal imaging device, as previously described, allows an image of the patient to be taken to determine if the radiation being supplied is accurately reaching the target treatment area. The image, e.g., an EPI, is suitably processed via the processing unit 18 and displayed via display unit 70 for analysis by the therapist.

Figure 3:
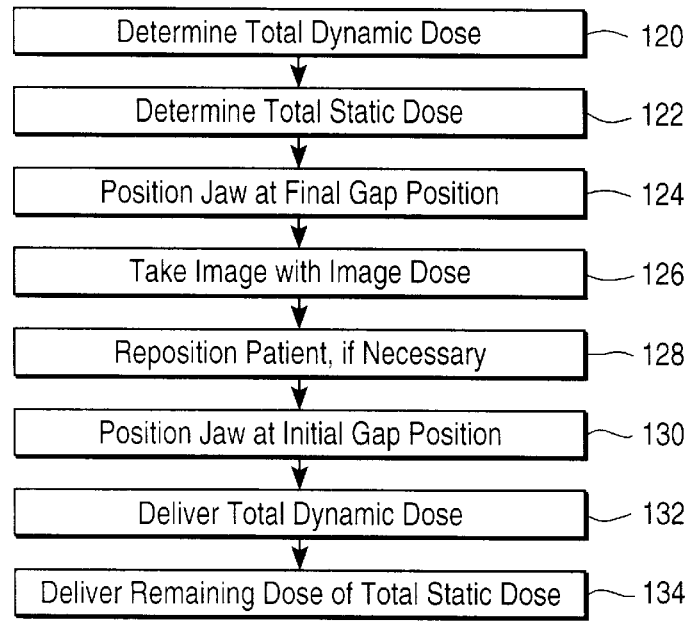
FIG. 3 illustrates a flow diagram of a process for portal imaging in a virtual wedge treatment in accordance with a preferred embodiment of the present invention.
Figure 4A:
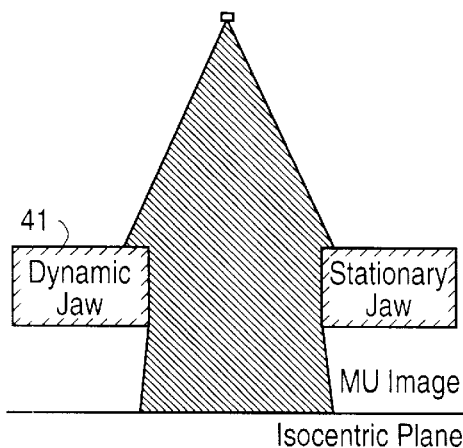
FIGS. 4a, 4b, 4c, and 4d illustrate portions of the virtual wedge treatment in accordance with the flow diagram of FIG. 3.
Figure 4B:
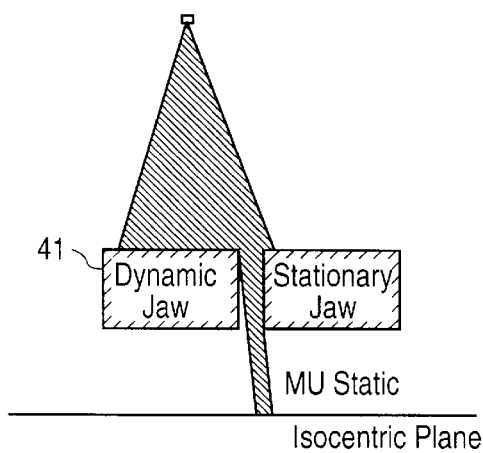
Figure 4C:
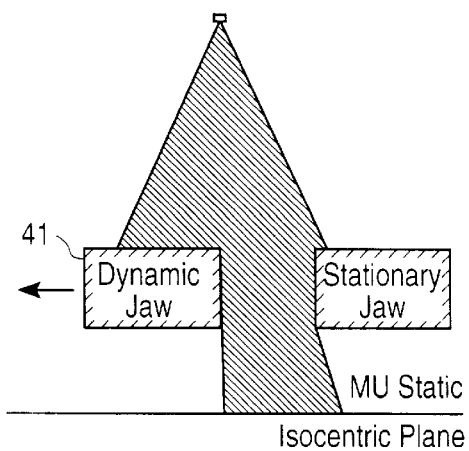
Figure 4D:
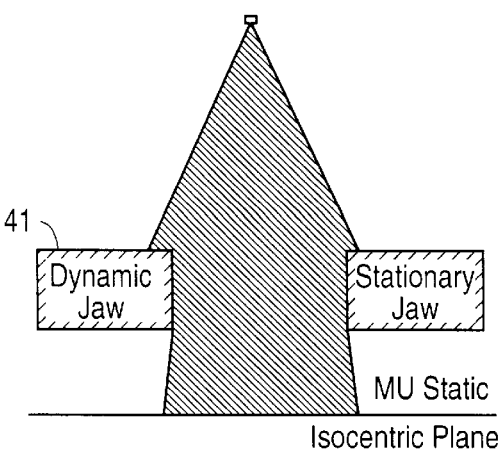

FIG. 3 illustrates a flow diagram representative of a preferred method of portal imaging during virtual wedge treatment through the treatment processing unit in accordance with the present invention. In a similar manner to prior virtual wedge techniques, a total treatment dose to be provided during a dynamic portion and static portion of jaw positioning is determined (steps 120 and 122). Then, rather than positioning the jaws, e.g., 41 and 42, at their initial gap position following pretreatment jaw calibration, as is conventionally done, the dynamic jaw, e.g., 41, is positioned in the final gap position indecated at 43 (step 124) in the present invention, as represented by FIG. 4a. The portal image is then taken by delivering a dose, $MU_{image}$, required for the imaging device 80 (FIG. 2), e.g., 10 MUs, (step 126). Once the image is taken, appropriate adjustment of the patient positioning may then occur, if necessary, (step 128). The jaws are then positioned at their initial gap position (step 130), as shown by FIG. 4b indecated at 45, e.g., by moving dynamic jaw 41 inward. The total dynamic dose, $MU_{jaw}$, is then supplied (step 132) by moving the dynamic jaw 41 from the initial gap position to the final position at a constant average speed, as further represented by FIG. 4c indicated 47, and as is well understood by those skilled in the art. Once the final gap position is reached indicated 43, a remaining dose for the treatment, $MU_{static}$, is supplied (step 134), as represented by FIG. 4d.

Thus, through the present invention, a portion of the dose supplied during a static portion of a virtual wedge treatment is delivered as an initial dose to allow capture of a portal image. Since the portal image is advantageously produced prior to a dynamic portion of the virtual wedge treatment, better utilization of the portal image can be made to correct for patient positioning errors.

FIGS. 5a and 5b present static MU calculations for two 50 MU (dose), 3 megavolt (MV) (energy of the beam), 60 degree (wedge angle) virtual wedge treatments to further illustrate that use of the present invention is capable even under worst case virtual wedge treatment conditions. What is meant by worst case in the context of the specification is a low amount of MU during the open field part of the treatment. For the calculations of FIG. 5a, a treatment field size of 50 mm (millimeter) is considered, while for FIG. 5b, a larger treatment field size of 200 mm is considered. Typically, a small treatment field such as 50 mm requires less than about 20 MUs for EPI. As illustrated, the 50 mm virtual wedge in FIG. 5a has 38.5 MU at Dmax and central axis, i.e., the static portion of the virtual wedge treatment. Accordingly, enough dosage is supplied at the static position to accommodate providing an image dose before the dynamic portion for portal imaging in accordance with the present invention.

Accordingly, a large treatment area such as 200 MV shown at FIG. 5b typically requires less than about 10 MUs for portal imaging. The 200 mm virtual wedge treatment condition has 17.5 MU at Dmax and central axis, again clearly accommodating provision of an image dose before the dynamic portion for portal imaging.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for virtual wedge treatment with portal imaging during radiation treatment by a radiation-emitting device, the method comprising:

utilizing an image dose with a static jaw gap position to initiate a virtual wedge treatment with portal imaging;

continuing with the virtual wedge treatment from a reduced jaw gap position with a dynamic dose and dynamic jaw positioning; and completing the virtual wedge treatment with a static dose in the static jaw gap position.

2. The method of claim 1 wherein the static jaw gap position comprises a widest gap position necessary for the virtual wedge treatment.

3. The method of claim 1 further comprising repositioning a patient based on the portal imaging before the step of continuing with the virtual wedge treatment.

4. The method of claim 1 wherein the step of continuing further comprises moving a dynamic jaw to the reduced jaw gap position.

5. The method of claim 1 wherein the image dose, the dynamic dose, and the static dose comprise a total dose desired for the virtual wedge treatment.

6. The method of claim 1 wherein dynamic jaw positioning further comprises moving a dynamic jaw from the reduced jaw gap position to the static jaw gap position.

7. A method for virtual wedge treatment that includes portal imaging for improved radiation therapy, the method comprising:

initiating the virtual wedge treatment with a dynamic jaw in a static jaw gap position;

providing an image dose to take a portal image;

adjusting a patient position based on the portal image;

moving the dynamic jaw to an initial jaw gap position;

providing a dynamic dose while moving the dynamic jaw from the initial jaw gap position to the static jaw gap position; and providing a static dose in the static jaw gap position to complete the virtual wedge treatment.

8. The method of claim 7 wherein the image dose depends on a portal imaging device used to take the portal image.

9. The method of claim 7 further comprising determining a total dose in the static jaw gap position.

10. The method of claim 9 wherein the total dose comprises the image dose and the static dose.

11. The method of claim 10 wherein the total dose and the dynamic dose comprise a desired treatment dose for the virtual wedge treatment.

* * * * *